(12) United States Patent
Nakanishi et al.

(10) Patent No.: US 10,745,614 B2
(45) Date of Patent: Aug. 18, 2020

(54) RARE-EARTH COMPLEX POLYMER

(71) Applicants: NATIONAL UNIVERSITY CORPORATION HOKKAIDO UNIVERSITY, Sapporo-shi, Hokkaido (JP); Tokyo University of Science Foundation, Tokyo (JP)

(72) Inventors: Takayuki Nakanishi, Sapporo (JP); Yuichi Hirai, Sapporo (JP); Yasuchika Hasegawa, Sapporo (JP); Yuichi Kitagawa, Sapporo (JP); Koji Fushimi, Sapporo (JP)

(73) Assignee: NATIONAL UNIVERSITY CORPORATION HOKKAIDO UNIVERSITY, Sapporo-shi, Hokkaido (JP)

( * ) Notice: Subject to any disclaimer, the term of this patent is extended or adjusted under 35 U.S.C. 154(b) by 0 days.

(21) Appl. No.: 16/098,297

(22) PCT Filed: Apr. 26, 2017

(86) PCT No.: PCT/JP2017/016574
§ 371 (c)(1),
(2) Date: Nov. 1, 2018

(87) PCT Pub. No.: WO2017/191795
PCT Pub. Date: Nov. 9, 2017

(65) Prior Publication Data
US 2019/0119567 A1 Apr. 25, 2019

(30) Foreign Application Priority Data

May 2, 2016 (JP) .................................. 2016-092667

(51) Int. Cl.
*C09K 11/06* (2006.01)
*C07C 49/92* (2006.01)
(Continued)

(52) U.S. Cl.
CPC .............. *C09K 11/06* (2013.01); *C07C 49/92* (2013.01); *C07F 5/003* (2013.01);
(Continued)

(58) Field of Classification Search
CPC ......... C09K 11/06; C07C 49/92; C07F 5/003; C07F 9/65515; C07F 15/00
See application file for complete search history.

(56) References Cited

U.S. PATENT DOCUMENTS 8,975,385 B2 * 3/2015 Hasegawa ............. C07F 9/5329
534/15

FOREIGN PATENT DOCUMENTS

| WO | 2011/013520 A1 | 2/2011 |
| WO | 2012/150712 A1 | 11/2012 |

OTHER PUBLICATIONS

Hirai, Yuichi et al., "Photophysical Properties of Eu(III) Complexes Bridged by Thiophene Derivatives," 66 Kidorui 80 (2015).*

(Continued)

*Primary Examiner* — Nicholas E Hill
(74) *Attorney, Agent, or Firm* — Sughrue Mion, PLLC

(57) ABSTRACT

Disclosed is a rare-earth complex polymer including trivalent rare-earth ions and a phosphine oxide bidentate ligand represented by the formula (1). One phosphine oxide bidentate ligand is coordinated to the two rare-earth ions, and crosslinks the same.

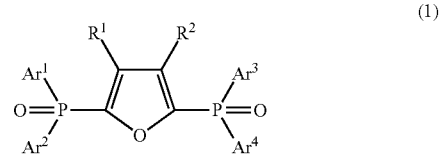

(1)

4 Claims, 5 Drawing Sheets

(51) Int. Cl.
  *C07F 5/00* (2006.01)
  *C08G 79/14* (2006.01)
  *C07F 9/655* (2006.01)
  *C07F 15/00* (2006.01)
  *C08G 79/04* (2006.01)
  *C07F 9/6553* (2006.01)
  *C07F 9/6561* (2006.01)

(52) U.S. Cl.
  CPC .......... *C07F 9/65515* (2013.01); *C07F 15/00* (2013.01); *C08G 79/04* (2013.01); *C08G 79/14* (2013.01); *C07F 9/6561* (2013.01); *C07F 9/655345* (2013.01); *C09K 2211/145* (2013.01); *C09K 2211/1458* (2013.01); *C09K 2211/182* (2013.01)

(56) References Cited

OTHER PUBLICATIONS

English-language SciFinder Scholar Abstract for Hirai, Yuichi et al., "Photophysical Properties of Eu(III) Complexes Bridged by Thiophene Derivatives," 66 Kidorui 80 (2015).*
CAS Registry No. 959298-05-6, [online], retrieved on May 29, 2017 from STN (total 3 pages).
International Search Report dated Jun. 13, 2017, issued by the International Searching Authority in application No. PCT/JP2017/016574.
International Preliminary Report on Patentability dated Nov. 8, 2018, issued by the International Searching Authority in application No. PCT/JP2017/016574.

* cited by examiner

RARE-EARTH COMPLEX POLYMER

CROSS REFERENCE TO RELATED APPLICATIONS

This application is a National Stage of International Application No. PCT/JP2017/016574 filed Apr. 26, 2017, claiming priority based on Japanese Patent Application No. 2016-092667 filed May 2, 2016.

TECHNICAL FIELD

The present invention relates to a rare-earth complex polymer.

BACKGROUND ART

Conventionally, rare-earth complex polymers that functions as a light emitting material has been suggested (for example, Patent Literature 1).

CITATION LIST

Patent Literature

Patent Literature 1: International Publication No. 2012/150712

SUMMARY OF INVENTION

Technical Problem

One aspect of the present invention is to provide a rare-earth complex polymer which has both of a light emitting property with excitation light and a light emitting property with shear stress stimulation, and further shows excellent solubility for solvents.

Solution to Problem

Inventors of the present invention found that, by using a specific phosphine oxide bidentate ligand having furan ring, a rare-earth complex polymer which has a light emitting property with excitation light and shear stress stimulation, and a favorable solubility can be obtained. One aspect of the present invention is based on those findings.

Namely, one aspect of the present invention relates to a rare-earth complex polymer including trivalent rare-earth ions and a phosphine oxide bidentate ligand represented by the formula (1) in which one phosphine oxide bidentate ligand is coordinated to the two rare-earth ions and cross-links the two rare-earth ions.

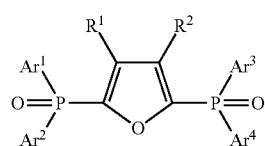

In the formula (1), $R^1$ and $R^2$ each independently represent a hydrogen atom or a monovalent organic group, and $Ar_1$, $Ar^2$, $Ar^3$, and $Ar^4$ each independently represent a monovalent aromatic group which may have a substituent group. $R^1$ and $R^2$ may bond to each other, and two groups selected from $Ar^1$, $Ar^2$, $Ar^3$, and $Ar^4$ may bond to each other.

Advantageous Effects of Invention

According to the present invention, a rare-earth complex polymer which has both of a light emitting property with excitation light and a light emitting property with shear stress stimulation, and further shows excellent solubility for a solvent can be provided.

DESCRIPTION OF EMBODIMENTS

Figure 1:
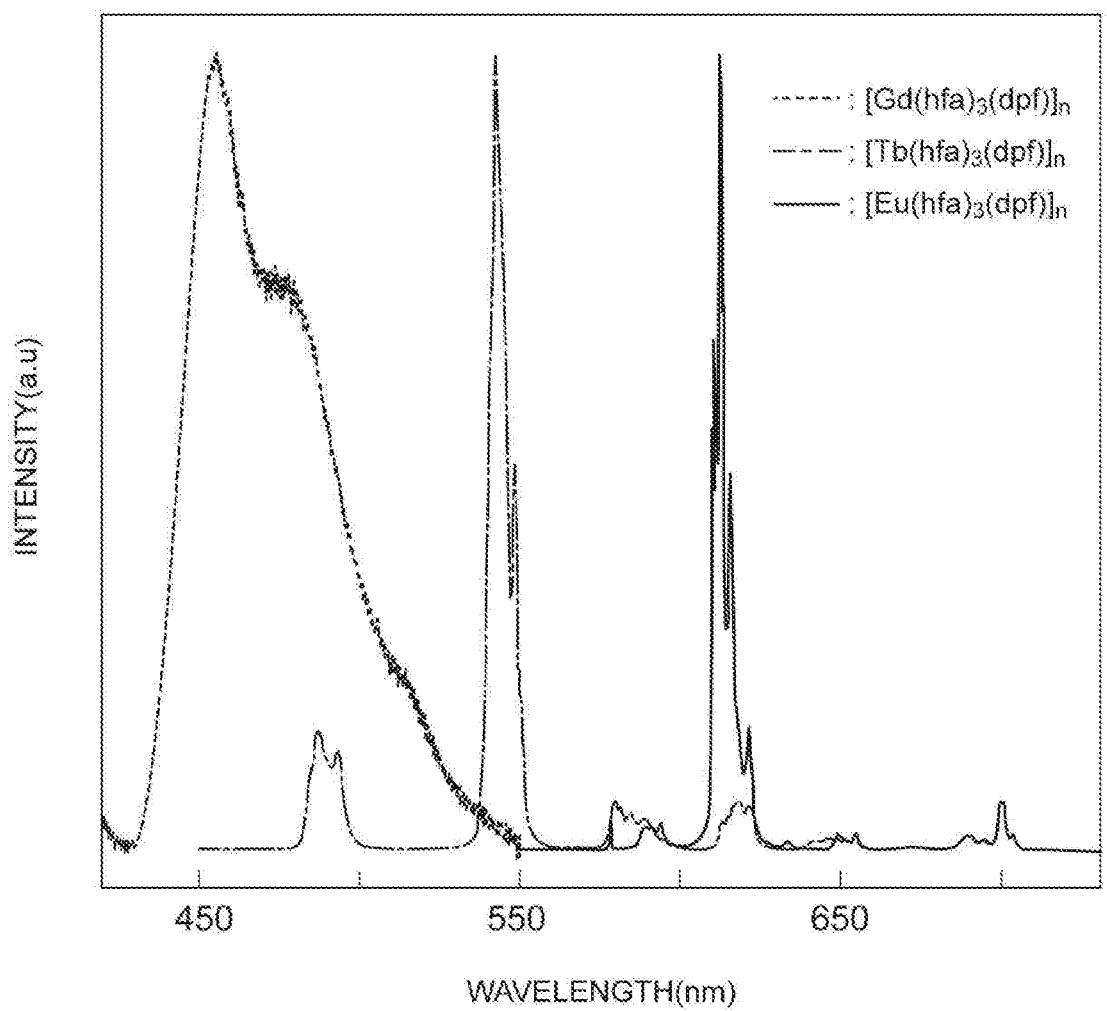
FIG. 1 is luminescence spectra of a rare-earth complex polymer having different rare-earth ions.

Hereinbelow, several embodiments of the present invention are described in detail. However, the present invention is not limited to the embodiments that are given below.

Rare-Earth Complex Polymer

A rare-earth complex polymer of the present embodiment includes trivalent rare-earth ions and a phosphine oxide bidentate ligand represented by the formula (1).

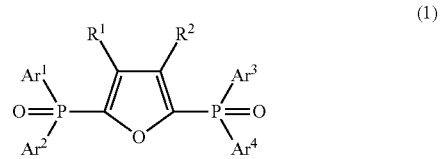

In the formula (1), $R^1$ and $R^2$ each independently represent a hydrogen atom or a monovalent organic group, and $Ar^1$, $Ar^2$, $Ar^3$, and $Ar^4$ each independently represent a monovalent aromatic group which may have a substituent group. $R^1$ and $R^2$ may bond to each other, and $Ar^1$, $Ar^2$, $Ar^3$, and $Ar^4$ may bond to one another.

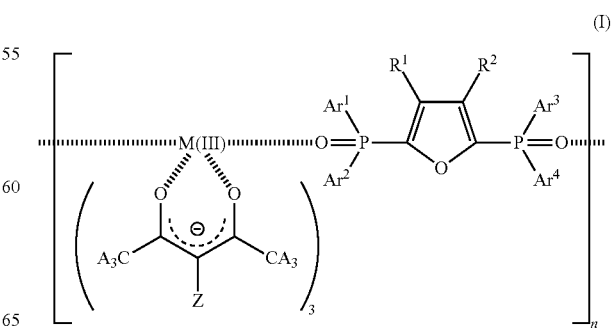

The formula (I) represents an exemplary repeating unit of a rare-earth complex polymer which includes a trivalent rare-earth ion M(III) and a phosphine oxide bidentate ligand represented by the formula (1). n in the formula is an integer representing the repeat number of the repeating unit. As two coordinatable sites contained in one phosphine oxide bidentate ligand of the formula (1) coordinate to two trivalent rare-earth ions (in the formula (I), M(III)) different from each other, thereby crosslinking the two rare-earth ions. As another phosphine oxide bidentate ligand coordinates to the rare-earth ion which has been coordinated with the phosphine oxide bidentate ligand, the rare-earth ions are crosslinked to one another in turn, and thus a rare-earth complex polymer is formed accordingly. To the rare-earth ion in the formula (I), a diketone ligand which will be described later is additionally coordinated. Thus, the rare-earth complex polymer described in the present specification indicates a coordinated polymer having a structure in which plural metal ions are linked via a coordination bond with ligand.

The trivalent rare-earth ion is not particularly limited, and can be suitably selected depending on desired luminescent color of the rare-earth complex polymer. The rare-earth ion can be at least one selected from the group consisting of Eu(III) ion, Tb(III) ion, Gd(III) ion, Sm(III) ion, Yb(II) ion, Nd(II) ion, Er(III) ion, Y(III) ion, Dy(III) ion, Ce(III) ion, and Pr(III) ion, for example. Among these, from a viewpoint of obtaining high luminescence intensity, the rare-earth ion may be at least one selected from the group consisting of Eu(III) ion, Tb(III) ion, and Gd(III) ion. The amount of the trivalent rare-earth ion to be included in the rare-earth complex polymer may be 0.1 to 20% by mass on the basis of the mass of the rare-earth complex polymer.

The trivalent rare-earth ion to be included in the rare-earth complex polymer may be either one kind or combination of any two or more kinds thereof. In a case in which the rare-earth complex polymer of the present embodiment includes two or more kinds of a rare-earth ion, by adjusting the ratio (molar ratio) of the rare-earth ions to be included in the rare-earth complex polymer, it is possible to obtain luminescence with intermediate color that is difficult to be obtained from a polymer including only one kind of the rare-earth ion. Accordingly, the luminescent color can be more finely adjusted. In accordance with a difference in irradiation of excitation light or shear stress stimulation, a difference in excitation wavelength, a difference in temperature, or the like, the rare-earth complex polymer including two or more kinds of a rare-earth ion exhibits luminescence with different color. Due to those reasons, by using two or more kinds of a rare-earth ion, various properties can be additionally given to the rare-earth complex polymer. As a result, characteristics as a security material can be further enhanced, for example.

Examples of the combination of two or more kinds of a rare-earth ion include Eu(III) and Tb(III), Eu(III) and Gd(III), and Tb(III) and Gd(III). In a case in which two or more kinds of the rare-earth ion (first rare-earth ion and second rare-earth ion) are combined, ratio of the second rare-earth ion relative to the first rare-earth ion ([mole number of the second rare-earth ion]/[mole number of the first rare-earth ion]) may be 0 to 1000, for example.

The monovalent organic group as $R^1$ or $R^2$ in the formula (1) is not particularly limited, and may be a hydrocarbon group having carbon number of 1 to 20, a hydroxyl group, a nitro group, an amino group, a sulfonyl group, a cyano group, a silyl group, a phosphonic acid group, a diazo group, a mercapto group, an alkoxy group, or a vinyl group, for example. $R^1$ and $R^2$ may bond to each other to form a divalent organic group. The divalent organic group formed by bonding between $R^1$ and $R^2$ may be a hydrocarbon group such as alkylene group or arylene group, for example. The carbon atom in the hydrocarbon group may be substituted with a divalent functional group such as a carbonyl group or an oxy group.

The monovalent aromatic group as $Ar^1$, $Ar^2$, $Ar^3$, or $Ar^4$ in the formula (1) is a group which consists of an aromatic ring having one bonding arm to be bound to a phosphorus atom, and the aromatic ring may additionally have a substituent group at a site other than the binding site for a phosphorus atom. Examples of the aromatic ring include a benzene ring, a thiophene ring, and a pyridine ring. Examples of the substituent group contained in the aromatic ring include a group that is the same as the monovalent organic group as $R^1$ or $R^2$, and a phosphine oxide group. In a case in which the aromatic ring constituting $Ar^1$, $Ar^2$, $Ar^3$, and $Ar^4$ has a phosphine oxide group as a substituent group, it may be coordinated to the rare-earth ion. Furthermore, two groups selected from $Ar^1$, $Ar^2$, $Ar^3$, and $Ar^4$ (for example, $Ar^1$ and $Ar^3$, $Ar^2$ and $Ar^4$) may form a divalent group as they bond to each other, either directly or via a divalent linking group. Examples of the linking group include an alkylene group, an arylene group, and a carbonyl group.

$Ar^1$, $Ar^2$, $Ar^3$, and $Ar^4$ may be a group represented by the following formula (3).

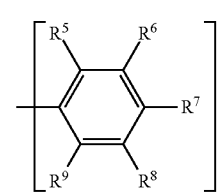

(3)

In the formula (3), $R^5$, $R^6$, $R^7$, $R^8$, and $R^9$ each independently represent a hydrogen atom, a hydrocarbon group having carbon number of 1 to 20, a hydroxyl group, a nitro group, an amino group, a sulfonyl group, a cyano group, a silyl group, a phosphonic acid group, a diazo group, a mercapto group, an alkoxy group, or a vinyl group.

From a viewpoint of the stability of the rare-earth complex polymer, the rare-earth ion constituting the rare-earth complex polymer may be coordinated with another plural ligands, in addition to the phosphine oxide bidentate ligand described above. Another ligand can be a multidentate ligand in order to increase the luminescence intensity of the rare-earth complex polymer. The multidentate ligand may be a diketone ligand represented by the following formula (2), for example. The diketone ligand can have a light sensitizing action.

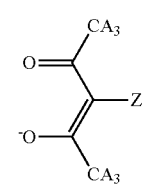

(2)

In the formula (2), A represents a hydrogen atom or a halogen atom, and Z represents a hydrogen atom or a deuterium atom. Plural As in the same molecule may be the same or different from each other.

In a crystal of the rare-earth complex polymer which includes the phosphine oxide bidentate ligand represented by the formula (1) and the multidentate ligand, plural polymer chains are easily arranged such that the multidentate ligands closely face each other. As there are plural sites at which the multidentate ligands having light sensitizing action face each other, the luminescence intensity of light emission caused by shear stress stimulation (triboluminescence) tends to increase more.

To further enhance the luminescence intensity and durability against light, the rare-earth complex polymer may include a rare-earth ion which forms a coordination structure of octacoordination or more including two or more phosphine oxide bidentate ligands and two or more diketone ligands.

The rare-earth complex polymer of the present embodiment can be synthesized by, for example, a method in which a rare-earth metal compound as a rare-earth ion source material and a phosphine oxide bidentate ligand having a structure represented by the formula (1) are stirred in a solvent capable of dissolving or dispersing the rare-earth metal compound and the phosphine oxide bidentate ligand, in the presence of a catalyst, if necessary. As for the solvent, a mixture of solvents that are suitable for each of the rare-earth metal compound and a compound to be a ligand may be used. For example, methanol, a mixture solvent of dichloromethane/methanol, or the like can be applied. As for the catalyst, for example, trimethylamine, lithium hydroxide, or the like can be added, if necessary. Temperature for the synthesis can be −80 to 70° C.

With regard to the synthesis of the rare-earth complex polymer, blending ratio between the rare-earth metal compound as a rare-earth ion source material and the phosphine oxide bidentate ligand ([mole number of rare-earth metal compound]:[mole number of phosphine oxide bidentate ligand]) may be 1:0.5 to 1:5, or 1:0.77 to 1:1. In a case in which a rare-earth complex polymer including two or more kinds of the rare-earth ion is to be synthesized, two or more kinds of a rare-earth metal compound including them can be combined at any ratio.

The rare-earth complex polymer of the present embodiment has, in addition to a light emitting property with excitation light, a light emitting property with shear stress stimulation, and further shows excellent solubility for a solvent. Because the rare-earth complex polymer of the present embodiment has a narrow full width at half maximum of a peak observed from a spectrophotometric spectrum, the rare-earth complex polymer can exhibit beautiful luminescent color in accordance with the rare-earth ion. Furthermore, by combining two or more kinds of the rare-earth ion, the luminescent color can be easily adjusted and also a luminescent color dependent on an excitation method can be obtained. A rare-earth complex polymer having those characteristics is useful, for example, as a security material which gives encrypted information to various materials such as plastic materials.

The rare-earth complex polymer of the present embodiment has excellent solubility and characteristics as a fluorophore. Due to those reasons, the rare-earth complex polymer can be also easily used as a fluorophore to be blended in various plastic materials.

In a case in which the rare-earth complex polymer is contained in a plastic material, for example, the rare-earth complex polymer is dissolved in advance in a solvent to prepare a polymer solution, and the solution is mixed with a plastic material or the like. By applying a solution containing the rare-earth complex polymer according to the present embodiment to a plastic material or the like, a plastic material and a plastic molded article in which the rare-earth complex polymer is homogeneously distributed can be easily obtained. The plastic molded article to be obtained can have high transparency.

Examples of a solvent in which the rare-earth complex polymer can be dissolved well include methanol and acetone.

The plastic material in which the rare-earth complex polymer is blended is not particularly limited. Examples of the plastic material include a polyethylene resin, a polypropylene resin, a polyvinyl chloride resin, a urea resin, a fluororesin, a polyester resin, a polyamide resin, a polyacetal resin, a polycarbonate resin, a polyarylate resin, a polysulfone resin, a polyphenylene sulfide resin, a polyethersulfone resin, a polyarylsulfone resin, a polytetrafluoroethylene resin, a phenol resin, a unsaturated polyester resin, an epoxy resin, a polyimide resin, and a polyamideimide resin.

A method for blending and mold-processing the rare-earth complex polymer is not particularly limited, and examples thereof includes injection molding, blow molding, compression molding, extrusion molding, reaction molding, hollow molding, heat molding, and FRP molding.

EXAMPLES

Hereinbelow, the present invention is specifically described based on the examples. However, the present invention is not limited to the following examples.

1. Synthesis of 2,5-bis(diphenylphosphoryl)furan (dpf)

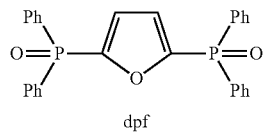 [SMILES: O=P(c1ccccc1)(c1ccccc1)c1ccc(P(=O)(c2ccccc2)c2ccccc2)o1]

dpf

To a flask, 2 mL (18.7 mol) of 2,5-dibromofuran and 60 mL of diethyl ether were added and stirred. To the reaction solution, 29 mL (46 mol) of n-butyl lithium was added at −78° C., and under stirring for 3 hours, the temperature was raised to −20° C. Thereafter, the reaction solution was cooled again to −78° C., added with 8.5 mL (46 mol) of chlorodiphenyl phosphine, and stirred for 8 hours. From the reaction solution, the product was extracted by using dichloromethane followed by dehydration. From the dehydrated solution, the solvent was removed. The product obtained by removing the solvent was dissolved in 30 mL of dichloromethane and cooled to 0° C. To the cooled reaction solution, 25 mL of hydrogen peroxide was added and stirred for 2 hours. From the reaction solution, the product was extracted by using dichloromethane followed by dehydration. From the dehydrated solution, the solvent was removed, and, by carrying out recrystallization, 3.8 g of the crystals of 2,5-bis(diphenylphosphoryl)furan (dpf) were obtained.

2. Production of Rare-Earth Complex Polymer

Preparation Example 1: [Eu(hfa)$_3$(dpf)]$_n$ Polymer (Eu 100%)

To a flask, 0.65 g of Eu(hfa)$_3$(H$_2$O)$_2$, 0.37 g of dpf, and 80 mL of methanol were added. The solution was refluxed for 3 hours at 60° C. under heating while stirred. Thereafter, precipitates in the reaction solution were separated, and then washed to obtain powder of a target rare-earth complex polymer.

Preparation Example 2: [Gd(hfa)$_3$(dpf)]$_n$ Polymer (Gd 100%)

Powder of a rare-earth complex polymer was obtained in the same manner as Preparation Example 1 except that Gd(hfa)$_3$(H$_2$O)$_2$ is used instead of Eu(hfa)$_3$(H$_2$O)$_2$.

Preparation Example 3: [Tb(hfa)$_3$(dpf)]$_n$ Polymer (Tb 100%)

Powder of a rare-earth complex polymer was obtained in the same manner as Preparation Example 1 except that Tb(hfa)$_3$(H$_2$O)$_2$ is used instead of Eu(hfa)$_3$(H$_2$O)$_2$.

Preparation Examples 4 to 6: [Tb, Eu(hfa)$_3$(dpf)]$_n$ Polymer (Tb/Eu=1, 10, 99)

Powder of a rare-earth complex polymer was obtained in the same manner as Preparation Example 1 except that Tb(hfa)$_3$(H$_2$O)$_2$ and Eu(hfa)$_3$(H$_2$O)$_2$ are used at a molar ratio of 1:1, 10:1 or 99:1 instead of Eu(hfa)$_3$(H$_2$O)$_2$.

3. Measurement of Shear Stress Luminescence Intensity, Durability Against Heat, and Luminescence Efficiency Intensity of luminescence (shear stress luminescence) caused by shear stress stimulation was measured for the [Eu(hfa)$_3$(dpf)]$_n$ polymer, [Eu(hfa)$_3$(dpt)]$_n$ polymer having thiophene ligand (dpt) represented by the following formula, and [Eu(hfa)$_3$(dpedot)]$_n$ polymer having EDOT ligand (dpedot) represented by the following formula.

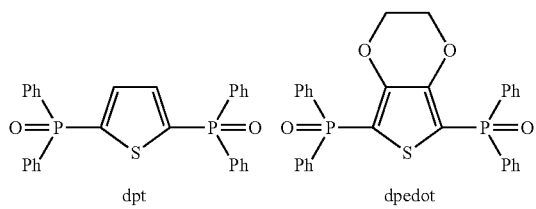

Luminescence of the rare-earth complex polymer at the time of rotating a stirring bar at constant revolution number after adding a rare-earth complex polymer and a stirring bar to a flask was collected by a CCD camera and the luminescence was integrated to obtain the sheer stress luminescence spectrum caused by pulverization. It remains the same for other examples of evaluating shear stress luminescence.

The [Eu(hfa)$_3$(dpf)]$_n$ polymer including a ligand having a furan group exhibited higher shear stress luminescence intensity compared to the [Eu(hfa)$_3$(dpt)]$_n$ polymer and [Eu(hfa)$_3$(dpedot)]$_n$ polymer which include a ligand having other skeletons.

Durability against heat of each polymer and luminescence efficiency of light emission at the time of irradiation with excitation light having wavelength of 380 nm were measured. The durability against heat was evaluated based on thermal decomposition temperature (° C.), which has been measured by thermogravimetric measurement using a thermogravimetric analyzer (TGA). The evaluation results are shown in Table 1.

TABLE 1

| Rare-earth complex polymer | Thermal decomposition temperature (° C.) | Luminescence efficiency $\Phi_{Ln}$ (%) | Luminescence efficiency $\Phi_{tot}$ (%) |
|---|---|---|---|
| [Eu(hfa)$_3$(dpf)]$_n$ | 270 | 69 | 64 |
| [Eu(hfa)$_3$(dpt)]$_n$ | 310 | 82 | 72 |
| [Eu(hfa)$_3$(dpedot)]$_n$ | 270 | 75 | 69 |

Luminescence efficiency $\Phi_{Ln}$ indicates the luminescence efficiency at the time of direct excitation of a rare-earth ion itself of a polymer. Luminescence efficiency $\Phi_{tot}$ indicates the luminescence efficiency at the time of excitation of an organic ligand of a polymer. [Eu(hfa)$_3$(dpf)]$_n$ exhibited the characteristics equivalent to other polymers, in terms of any of the thermal decomposition temperature, luminescence efficiency $\Phi_{Ln}$, and luminescence efficiency $\Phi_{tot}$.

4. Solubility

Solubility for an organic solvent was measured for the [Eu(hfa)$_3$(dpf)]$_n$ polymer and [Eu(hfa)$_3$(dpedot)]$_n$ polymer. According to a test in which 30 mg of a rare-earth complex polymer and 2 mL of methanol are stirred in a glass container and the state of the mixed solution is observed, the solubility was evaluated.

As a result, the [Eu(hfa)$_3$(dpf)]$_n$ polymer was completely dissolved in methanol to obtain a transparent solution. On the other hand, the [Eu(hfa)$_3$(dpedot)]$_n$ polymer was just dispersed in methanol, and white precipitates were shown. The [Eu(hfa)$_3$(dpf)]$_n$ polymer exhibited luminescence under ultraviolet irradiation even in a dissolved state in methanol.

5. Measurement of Luminescence Color of Polymer with Different Kind of Metal Element Powder of the [Eu(hfa)$_3$(dpf)]$_n$ polymer, [Gd(hfa)$_3$(dpf)]$_n$ polymer, and [Tb(hfa)$_3$(dpf)]$_n$ polymer was irradiated with excitation light having wavelength of 380 nm, and then luminescence from the rare-earth complex polymer was measured. As a device for measuring the luminescence characteristics caused by UV excitation, HORIBA Fluorolog-3 spectrofluorometer was used. FIG. 1 is a luminescence spectrum of each rare-earth complex polymer.

As shown in FIG. 1, different fluorescent spectrum patterns were exhibited depending on the kind of a rare-earth element contained in the polymer. The luminescence color was red for the [Eu(hfa)$_3$(dpf)]$_n$ polymer, blue for the [Gd(hfa)$_3$(dpt)]$_n$ polymer, and green for the [Tb(hfa)$_3$(dpf)]$_n$ polymer. From those results, it was shown that the luminescence color of the polymer can be controlled by modifying the kind of a rare-earth element.

Figure 2:
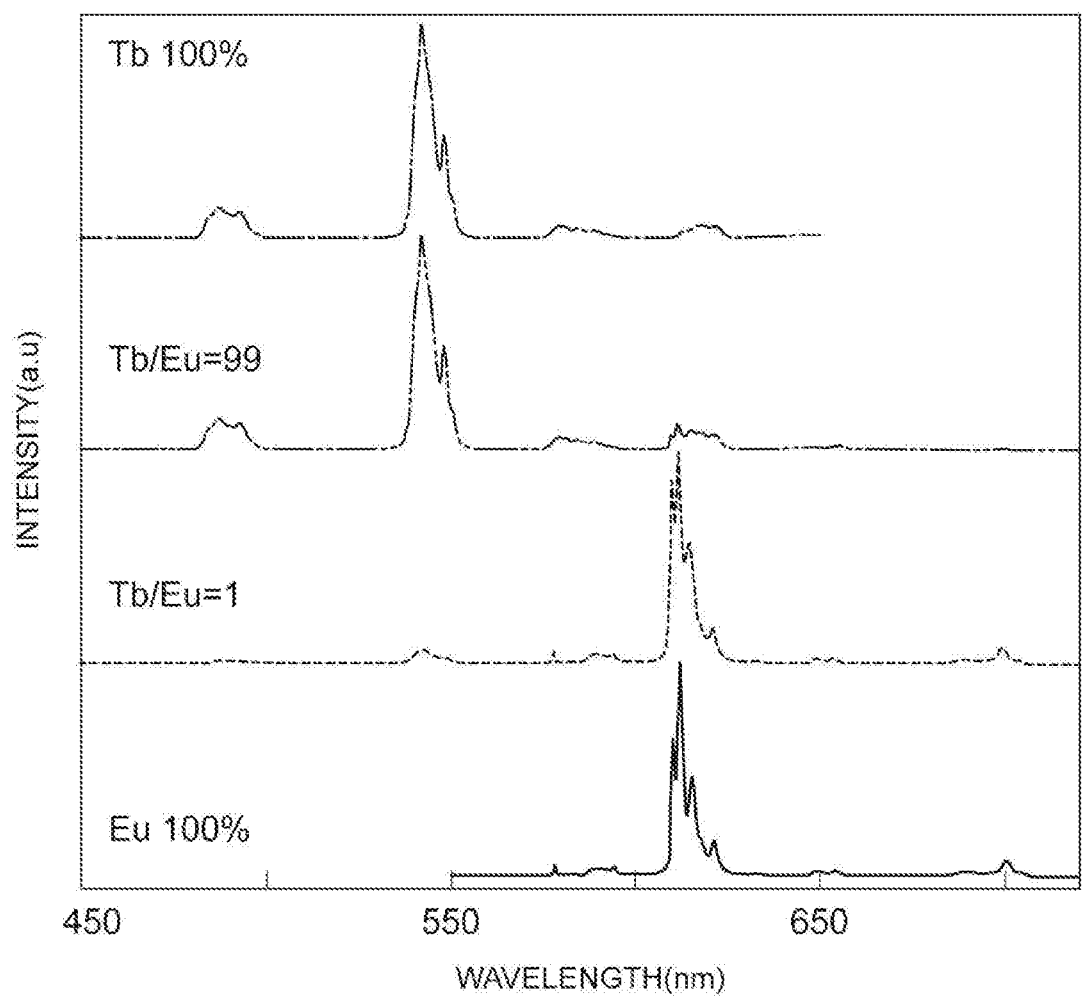
FIG. 2 is luminescence spectra of a rare-earth complex polymer with different ratios of rare-earth ions.

6. Measurement of Luminescence Color of Polymer with Different Ratio of Rare-Earth Element By using powder of the rare-earth complex polymer in which ratio between Eu and Tb (molar ratio, Eu:Tb) is 100:0, 1:1, 1:99, or 0:100, the shear stress luminescence was measured. FIG. 2 shows the luminescence spectra of each rare-earth complex polymer.

Fluorescence with red color (612 nm) was obtained from the [Eu(hfa)$_3$(dpf)]$_n$ polymer and fluorescence with green color (545 nm) was obtained from the [Tb(hfa)$_3$(dpf)]$_n$ polymer. Furthermore, according to modification of the ratio of a rare-earth element in the polymer, the intensity ratio of the fluorescence at 612 nm and 545 nm, which is exhibited by the polymer, varied, showing an intermediate color of red and green. From those results, it was shown that the luminescence color can be controlled by modifying the ratio of a rare-earth element in the polymer.

7. Influence of Excitation Method on Luminescence Color

Figure 3A:
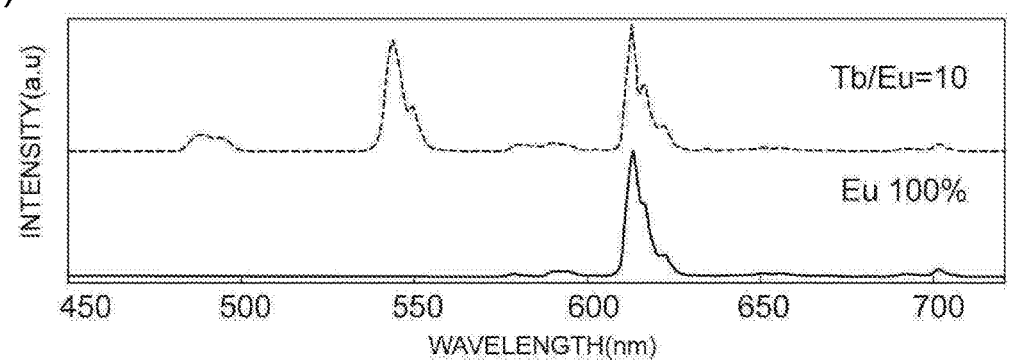
FIG. 3(a) is luminescence spectra obtained by irradiation of excitation light and FIG. 3(b) is luminescence spectra obtained by shear stress stimulation.
Figure 3B:
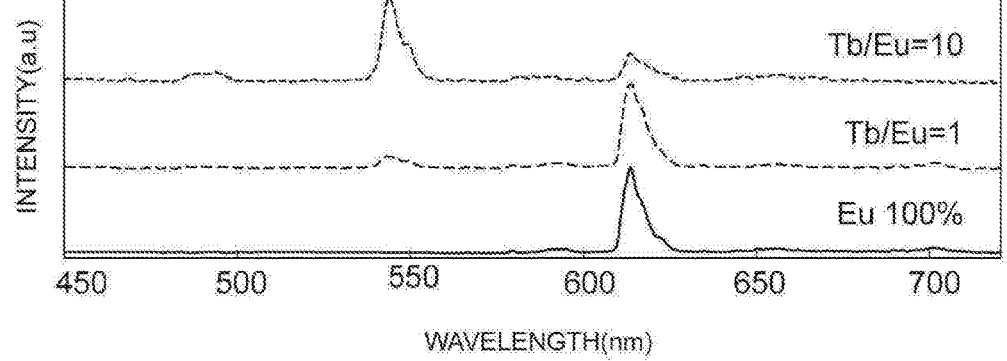

Powder of the [Eu(hfa)$_3$(dpf)]$_n$ polymer and [Tb, Eu(hfa)$_3$(dpf)]$_n$ polymer (Tb/Eu=1 or 10) was irradiated with excitation light having wavelength of 380 nm or applied with shear stress stimulation, and then luminescence from the polymer was measured. FIG. 3(a) shows luminescence spectra obtained by irradiation of excitation light and FIG. 3(b) shows luminescence spectra obtained by shear stress stimulation.

All polymers used for the measurement showed luminescence by an excitation method using excitation light or shear stress stimulation. In particular, the luminescence spectrum of the polymers which include two kinds of a rare-earth element was different depending on the excitation method. The polymer only including Eu emitted red light by an excitation method using excitation light or shear stress stimulation. The polymer with Tb/Eu=10 emitted yellow light by excitation light while emitting yellowish green light by shear stress stimulation. The polymer with Tb/Eu=1 emitted orange light by shear stress stimulation. It was shown from those results that, by modifying the ratio of a rare-earth element, the excitation method-dependent luminescence can be obtained from the polymer.

8. Influence of Temperature Condition on Luminescence Color

Figure 4:
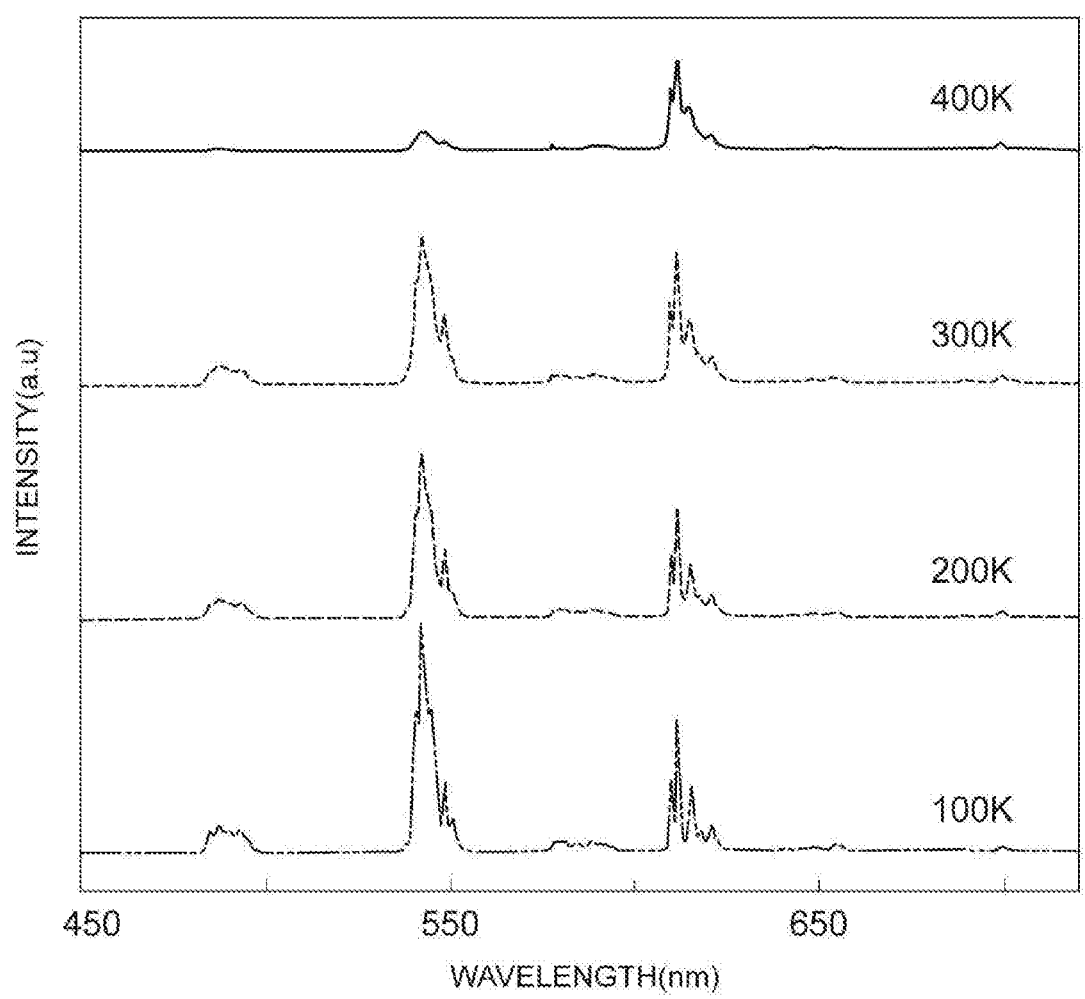
FIG. 4 is luminescence spectra of a rare-earth complex polymer ([Tb, Eu(hfa)$_3$(dpf)]$_n$ polymer (Tb/Eu=10)) at various temperature conditions.

Powder of the [Tb, Eu(hfa)$_3$(dpf)]$_n$ polymer (Tb/Eu=10) was irradiated with excitation light having wavelength of 380 nm, and then luminescence color depending on a difference in temperature condition was measured. The temperature condition was set at 100 K, 200 K, 300 K, or 400 K. FIG. 4 shows luminescence spectra of the polymer at each temperature condition.

Lower the temperature is, stronger the luminescence intensity at a wavelength of 545 nm was exhibited by the [Tb, Eu(hfa)$_3$(dpf)]$_n$ polymer (Tb/Eu=10). Meanwhile, higher the temperature is, stronger the luminescence intensity at a wavelength of 613 nm was exhibited. From those results, it was shown that the [Tb, Eu(hfa)$_3$(dpf)]$_n$ polymer has a luminescence wavelength which varies in accordance with temperature.

9. Influence of Excitation Wavelength on Luminescence Color

Figure 5A:
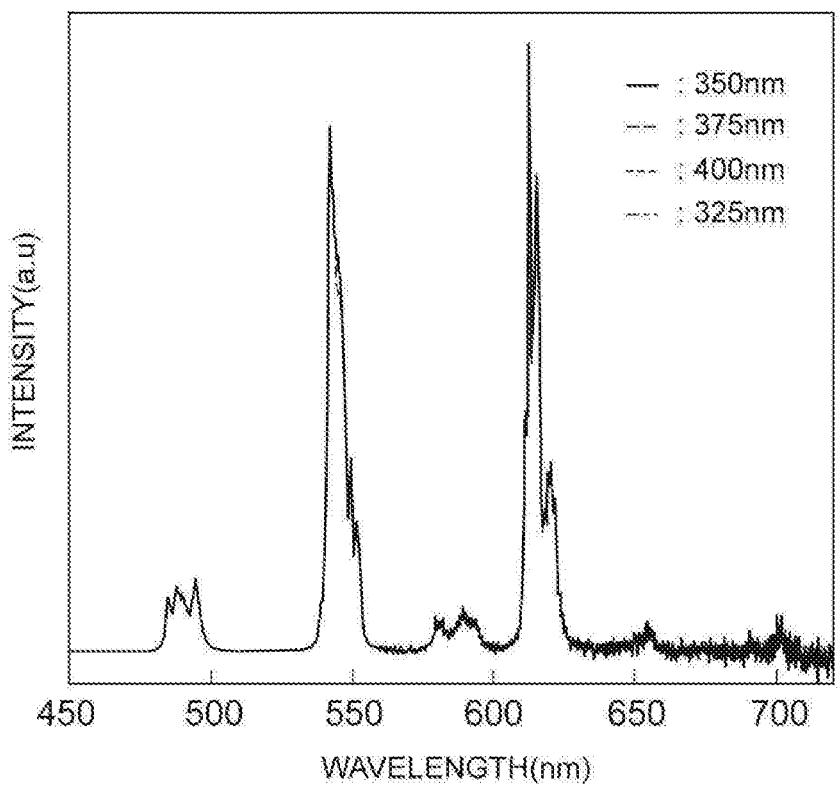
FIG. 5(a) is luminescence spectra of [Tb, Eu(hfa)$_3$(dpbp)]$_n$ polymer (Tb/Eu=150)
Figure 5B:
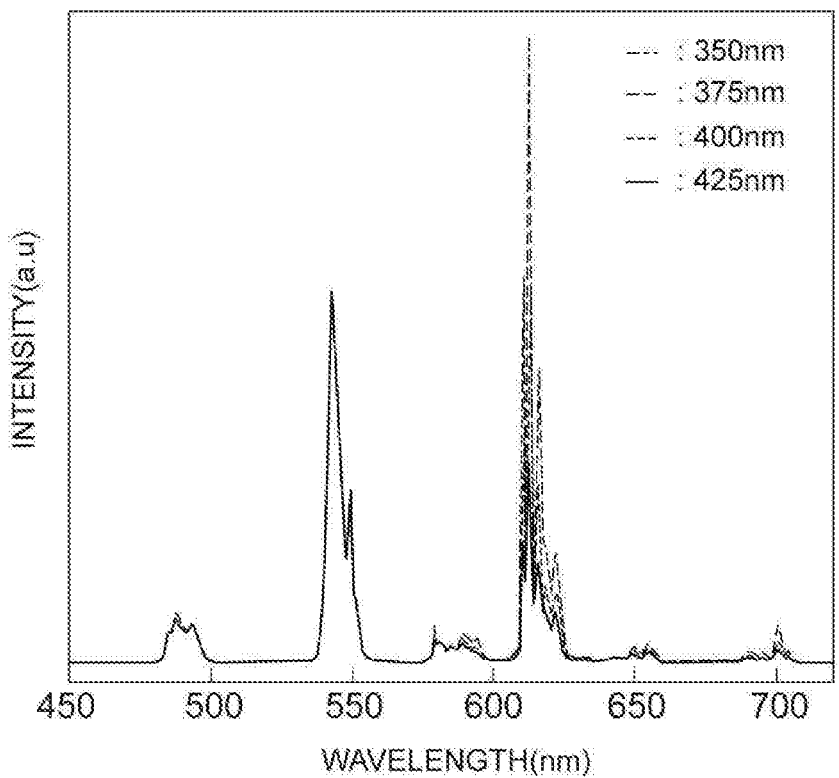
FIG. 5(b) is luminescence spectra of [Tb, Eu(hfa)$_3$(dpf)]$_n$ polymer (Tb/Eu=10) when irradiation is carried out with excitation light having different wavelength.

Powder of the [Tb, Eu(hfa)$_3$(dpbp)]$_n$ polymer (Tb/Eu=150) which has been crosslinked by 1,4-bis(diphenylphosphoryl)biphenyl (dpbp) and [Tb, Eu(hfa)$_3$(dpf)]$_n$ polymer (Tb/Eu=10) was irradiated with excitation light having wavelength of 350 nm, 375 nm, 400 nm, or 425 nm, and then luminescence from the polymer was measured. FIG. 5(a) shows luminescence spectra of the [Tb, Eu(hfa)$_3$(dpbp)]$_n$ polymer (Tb/Eu=150) and FIG. 5(b) shows luminescence spectra of the [Tb, Eu(hfa)$_3$(dpf)]$_n$ polymer (Tb/Eu=10).

The [Tb, Eu(hfa)$_3$(dpbp)]$_n$ polymer exhibited an identical luminescence spectrum by excitation light with any wavelength. Meanwhile, the [Tb, Eu(hfa)$_3$(dpf)]$_n$ polymer exhibited a luminescence spectrum which varies in accordance with the wavelength of excitation light, and a change in the luminescence spectrum was shown near 610 nm to 630 nm, in particular. From those results, it was shown that the [Tb, Eu(hfa)$_3$(dpf)]$_n$ polymer has a luminescence wavelength which varies in accordance with the wavelength of excitation light.

The invention claimed is:

1. A rare-earth complex polymer comprising:
   trivalent rare-earth ions; and
   a phosphine oxide bidentate ligand represented by the formula (1),
   wherein one phosphine oxide bidentate ligand is coordinated to the two rare-earth ions and crosslinks the two rare-earth ions,

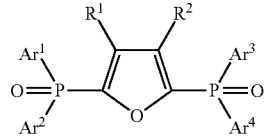

(1)

in the formula (1), R$^1$ and R$^2$ each independently represent a hydrogen atom or a monovalent organic group, Ar$^1$, Ar$^2$, Ar$^3$, and Ar$^4$ each independently represent a monovalent aromatic group which may have a substituent group, R$^1$ and R$^2$ may bond to each other, and two groups selected from Ar$^1$, Ar$^2$, Ar$^3$, and Ar$^4$ may bond to each other.

2. The rare-earth complex polymer according to claim 1, comprising two or more kinds of the rare-earth ion.

3. The rare-earth complex polymer according to claim 1, wherein the rare-earth ion is at least one rare-earth ion selected from the group consisting of Eu(III) ion, Tb(III) ion, Gd(III) ion, Sm(III) ion, Yb(III) ion, Nd(III) ion, Er(III) ion, Y(III) ion, Dy(III) ion, Ce(III) ion, and Pr(III) ion.

4. The rare-earth complex polymer according to claim 1, further comprising a diketone ligand coordinated to the rare-earth ion represented by the formula (2),

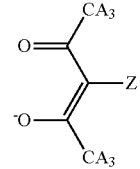

(2)

in the formula (2), A represents a hydrogen atom or a halogen atom, Z represents a hydrogen atom or a deuterium atom, and a plurality of As in the same molecule may be the same or different from each other.

* * * * *